United States Patent [19]
Bahmanyar et al.

[11] Patent Number: 6,066,128
[45] Date of Patent: May 23, 2000

[54] MULTI-SPOT LASER SURGERY

[75] Inventors: Sina Bahmanyar, Rockford, Ill.; Mark S. Jones, Ballwin, Mo.

[73] Assignee: Alcon Laboratories, Inc.

[21] Appl. No.: 09/241,208

[22] Filed: Feb. 1, 1999

Related U.S. Application Data

[62] Division of application No. 08/556,204, Nov. 9, 1995, Pat. No. 5,921,981.

[51] Int. Cl.⁷ ..................................................... A61B 17/36
[52] U.S. Cl. .................................. 606/4; 606/17; 606/16
[58] Field of Search ................................. 606/4, 5, 6, 10, 606/11, 12, 14, 15, 16, 17, 19; 372/108

[56] References Cited

U.S. PATENT DOCUMENTS

| | | |
|---|---|---|
| 4,477,159 | 10/1984 | Mizuno et al. . |
| 4,719,912 | 1/1988 | Wienberg . |
| 4,830,483 | 5/1989 | Kohayakawa et al. ...................... 606/4 |
| 5,007,729 | 4/1991 | Erickson et al. . |
| 5,067,951 | 11/1991 | Greve . |
| 5,189,450 | 2/1993 | Crossman et al. . |
| 5,300,062 | 4/1994 | Ueno .......................................... 606/4 |
| 5,309,187 | 5/1994 | Crossman et al. . |
| 5,318,022 | 6/1994 | Toboada et al. . |
| 5,437,658 | 8/1995 | Muller et al. ................................ 606/4 |
| 5,921,981 | 7/1999 | Bahmanyar et al. ........................ 606/4 |

*Primary Examiner*—Linda C. M. Dvorak
*Assistant Examiner*—Sonya Harris-Ogugua
*Attorney, Agent, or Firm*—Jeffrey S. Schira

[57] ABSTRACT

Various embodiments of optical fiber cables and laser probes are disclosed for providing multi-spot laser beams from a single laser beam source. This permits time-intensive but repetitive laser surgical procedures such as panretinal photocoagulation to be performed with increased accuracy and in a fraction of the time currently allotted for such procedures.

4 Claims, 4 Drawing Sheets

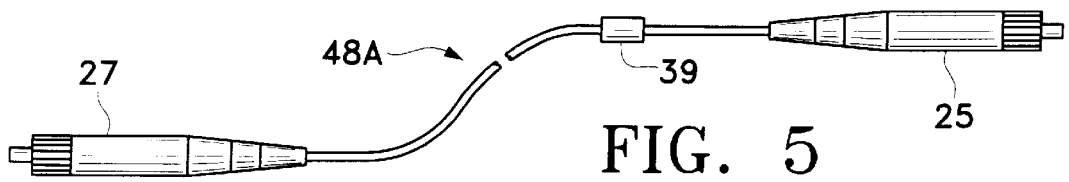
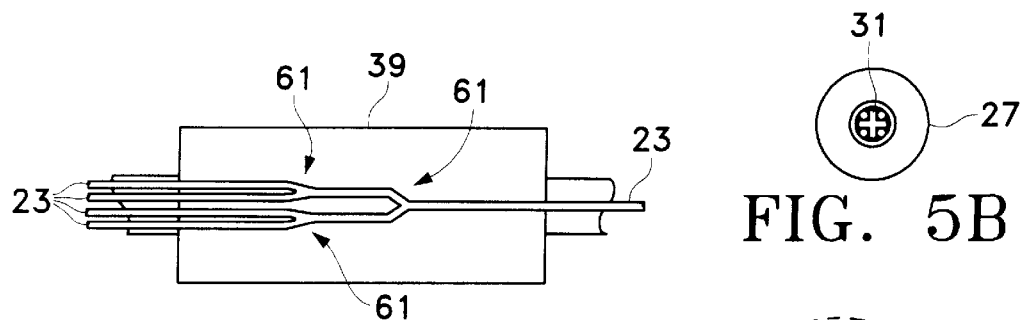 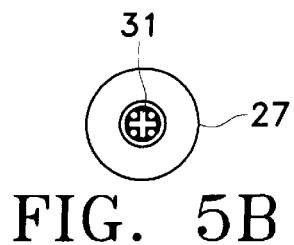
FIG. 5A     FIG. 5B
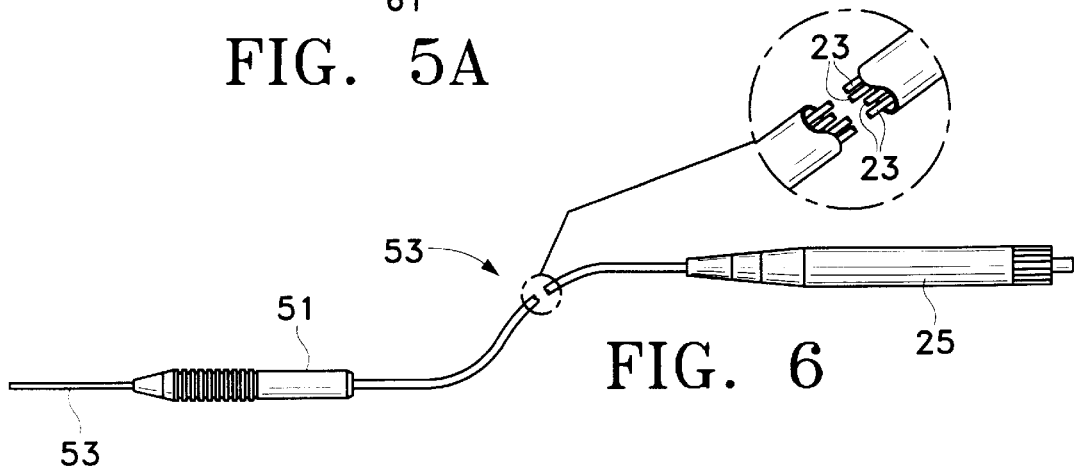
FIG. 6
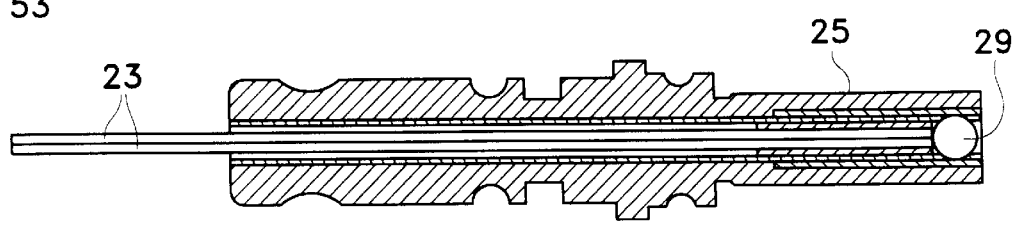
FIG. 6A
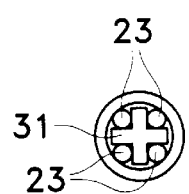 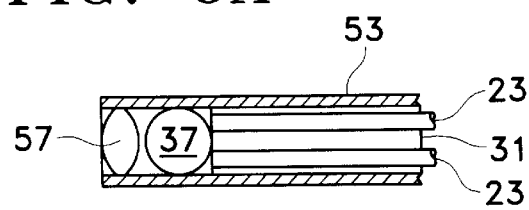
FIG. 6B     FIG. 6C

MULTI-SPOT LASER SURGERY

This application is a divisional of U.S. patent application Ser. No. 08/556,204, filed Nov. 9, 1995, now U.S. Pat. No. 5,921,981.

BACKGROUND OF THE INVENTION

This invention relates to laser ophthalmic surgery and more particularly to a method and system particularly suited to panretinal photocoagulation procedures performed on a human patient.

Photocoagulation has been used for various ophthalmic procedures such as panretinal photocoagulation (PRP) and the like. Such procedures are performed using either a slit-lamp (SL) laser delivery system or, when surgical intervention is required, endo-ocular laser probes.

In the slit-lamp system, laser energy is delivered from the laser source to the imaging optics via a single optical fiber. As is known, the imaging optics are used in conjunction with a variety of contact lenses, and must be capable of focusing the output end (distal) of the fiber onto the retina The focal length of the imaging optics, is typically variable, i.e. zoom, to magnify the size of the fiber's image on the retina from 1 to 20 times, corresponding to 50–1000 microns on the retina.

Current SL systems offer a single fiber for single point exposure on the surgical area. The surgeon positions the fiber image to the desired location by observing a low energy aiming beam on the treatment area. By turning the laser on/off and moving the aiming beam, the surgeon can lay down a pattern of spots on the treatment area. The number of spots is determined by the size of the treatment area and the laser spot size desired. For photocoagulation of microaneurysms on the retina, the laser spot size must be small (<100 microns) to avoid damage to surrounding tissue.

For medical conditions which require panretinal photocoagulation (PRP), also known as scatter photocoagulation, the area affected may include the entire retina outside the foveal region. The accepted mode of treatment is to lay down an uniform distribution of photocoagulative burns, with spot sizes of 250–500 microns and spaced at 1 times the spot diameter. A typical treatment consist of 1600 burns. The time to position the spot and deliver the laser energy depends on the features of the SL and the skill of the surgeon and is typically 2 seconds per spot. This means that the treatment time is in excess of 60 minutes which is fatiguing to the patient and surgeon. Also, laying down a uniform pattern is difficult and the pattern is typically more random than a geometric in distribution.

When PRP treatment requires surgical intervention, the SL is not used. Instead standard endoocular laser probes are employed. The treatment objectives are the same, however, to lay down a pattern of photocoagulative burns in the affected area. Using the endo-laser probe, the surgeon holds the distal tip close to the retina and lays down 1500–2000 spots, 500 microns in diameter. This procedure can take more than one hour. Using the probe close to the retina increases the risk of accidental tears and the length of the procedure prolongs the anesthesia time in high risk patient groups.

SUMMARY OF THE INVENTION

Among the various objects and features of the present invention may be noted the provision of an apparatus and method which facilitates ophthalmic operations such as panretinal photocoagulation.

Another object is the provision of such an apparatus and method which significantly reduces the time required for such operations.

A third object is the provision of such an apparatus and method which is readily usable with existing equipment.

A fourth object is the provision of such an apparatus and method which provides increased accuracy.

A fifth object is the provision of such an apparatus and method which provides a more repeatable pattern of laser spots or burns.

Other objects and features will be in part apparent and in part pointed out hereinafter.

Briefly, in a first aspect of the present invention, a method of performing an ophthalmic surgical procedure such as panretinal photocoagulation on a human patient includes the steps of:

(a) directing an aiming illumination beam onto the retina of the patient to define a target;

(b) transmitting a plurality of simultaneous laser beams onto the retina on the target;

(c) directing the aiming illumination beam to a new position on the retina to define an additional target in the eye of the patient; and (d) repeating steps (b) and (c).

In a second aspect of the present invention a multi-spot slit-lamp system for performing an ophthalmic surgical procedure such as panretinal photocoagulation on a human patient includes a source of illumination light, a laser source for generating a single beam of laser energy, and an optical system for directing the illumination light along an optical path to the eye of a patient to be treated. Structure is provided for splitting the single beam of laser energy into a plurality of simultaneous laser beams. The splitting structure has a distal end through which exit the simultaneous laser beams into the optical path of the illumination light. It is preferred that the simultaneous laser beams be generally parallel to each other and have a size suitable for performing the ophthalmic surgical procedure on a human patient.

In a third aspect of the present invention, a laser probe assembly for an ophthalmic surgical procedure such as panretinal photocoagulation on a human patient includes a proximal connector adapted for connection to a laser source, which laser source generates a single beam of laser energy. A handpiece having a distal end sized to fit inside the eye of a human patient for purposes of performing the ophthalmic surgical procedure is optically connected to the laser source connector by an optical fiber cable extending from the proximal connector to the handpiece. Structure for splitting the single beam of laser energy into a plurality of simultaneous laser beams is disposed between the laser source and the distal end of the handpiece so that the simultaneous laser beams exit from the distal end of the handpiece in a predetermined distribution. The simultaneous laser beams upon exiting from the distal end of the handpiece have a size suitable for performing said ophthalmic surgical procedure on a human patient.

BRIEF DESCRIPTION OF THE DRAWINGS

FIG. 5 is an elevation of a third embodiment of the optical fiber cable used in the system of FIG. 1;

FIG. 5A is an enlarged view with parts broken away for clarity of the optical fiber cable of FIG. 5;

FIG. 5B is an end view of the distal connector of the optical fiber cable of FIG. 5;

FIG. 6 is an elevation of a laser probe of the present invention adapted for ophthalmic surgical procedures such as panretinal photocoagulation;

FIG. 6A is a cross sectional view of the proximal connector of the laser probe of FIG. 6;

FIG. 6B is a distal end view of the probe of FIG. 6, with parts removed for clarity;

FIG. 6C is a cross sectional view of the distal end of the probe of FIG. 6;

Similar reference characters indicate similar parts throughout the several views of the drawings.

DESCRIPTION OF THE PREFERRED EMBODIMENT

Figure 1:
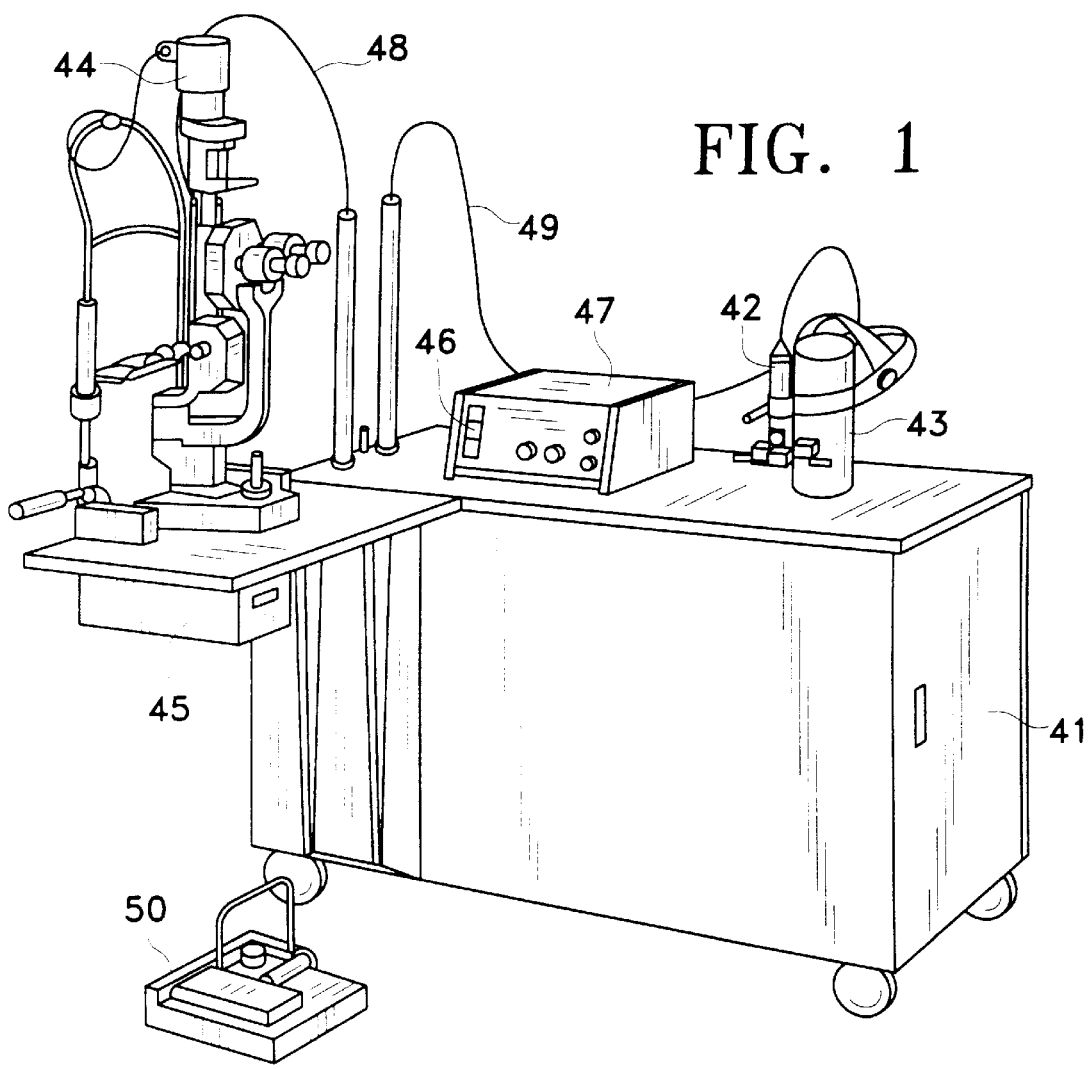
FIG. 1 is a perspective view of a slit-lamp laser system incorporating the present invention.
Figure 2:
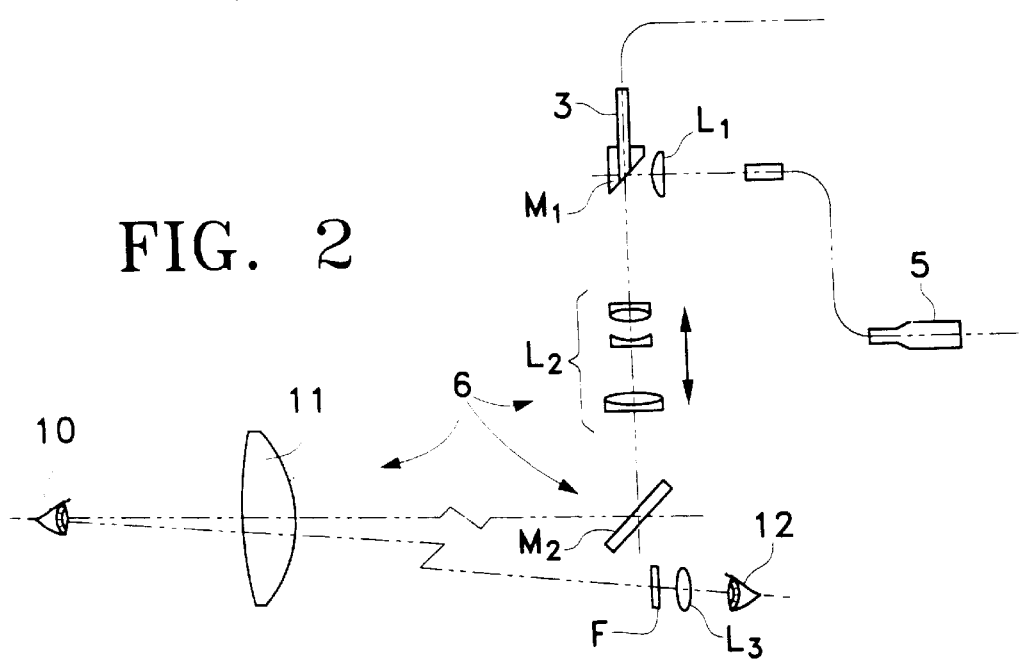
FIG. 2 is a simplified illustration of the optics of the system of FIG. 1.

In a first embodiment of the present invention, the ophthalmic operation is performed using a slit-lamp apparatus, such as that shown in FIGS. 1 and 2. The physician performing such an operation uses such apparatus to control the application (and intensity) of illuminating light and the application (and intensity) of laser energy to the treatment/operative site. Specifically, such apparatus includes an optical fiber device 3 for transmitting a laser beam coming from a laser source, and a second optical fiber device 5 for transmitting the illumination light from a light source. A lens holder unit 6 is provided for accommodating therein a lens system for transmitting the laser beam and the illumination light to the patient's eye 10. The optical system includes an ophthalmoscope lens 11 for magnifying the image of the fundus oculi of the patient's eye. This image is thereby provided to the eye 12 of the physician.

Referring more specifically to FIG. 2, the optical system includes a focusing lens L1 for the illumination light and a perforated mirror M1. These two components are arranged such that the laser beam travels generally along the optical path of the illumination light. (As will become apparent, the laser beam at this point is actually a composite beam, and it is the composite beam which travels along the optical path defined by the optics discussed below to the patient's eye.) It is possible to use a half mirror or a dichroic mirror in place of the perforated mirror M1.

The laser beam and the illumination light coaxial therewith are projected on the patient's eye by mean of a projection lens L2. The size of the spot of the laser beam imaging on the fundus oculi is changed by moving the projection lens L2 in the direction of optical axis. A mirror M2 is housed in the aforementioned lens holder unit 6 together with the aforementioned lens L1 and the mirror M1. A filter F for protecting the physician's eye 12 is adapted to be placed out of the path of light during the observation and the sighting, but is moved into the path of light in advance of the laser operation. A lens L3 is used for observing the image of the patient's eye.

FIG. 1 shows a slit-lamp in combination with a binocular indirect ophthalmoscope for permitting a switching of the laser beam. Specifically, a laser source housing 41 encases a laser tube, a laser control system and so forth. The binocular indirect ophthalmoscope 42 is mounted on a carrier 43. A slitlamp 44 is adapted to be moved up and down by means of a slit table 45. In conventional manner, change-over switches 46 and a control box 47 are provided, control box 47 controlling various conditions such as, for example, coagulation time, coagulation power and spot size of the laser beam. Optical cables 48, 49 for the laser beam are connected to ophthalmoscope 42 and to the slitlamp 44 respectively. A foot switch device 50 has two pedals for triggering the optical coagulation and for triggering the vertical movement of the slit table 45 respectively. It should be understood that also the slit-lamp system is shown and described in some detail, the present invention is not limited to any particular slit-lamp system.

Figure 3:
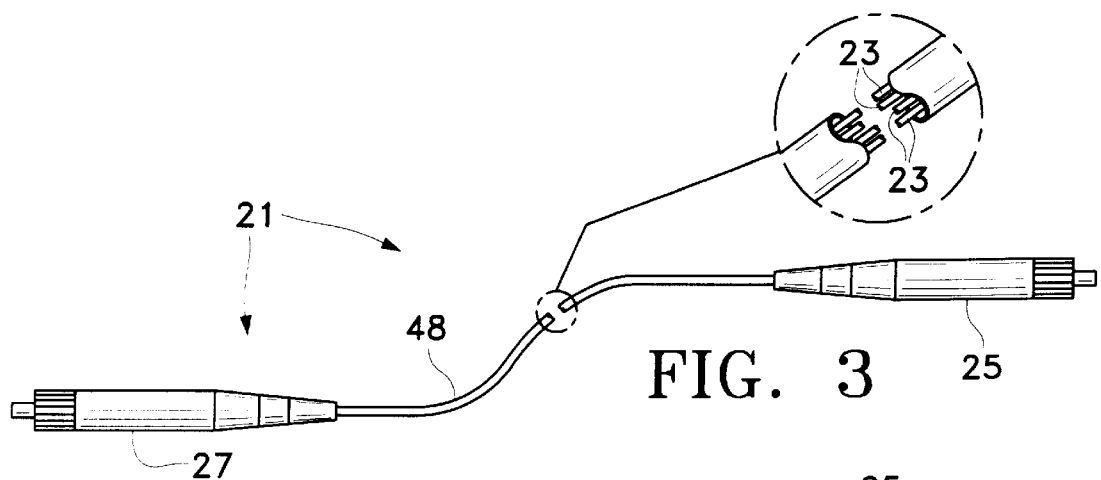
FIG. 3 is an elevation of an optical fiber cable used in the system of FIG. 1.
Figure 3A:
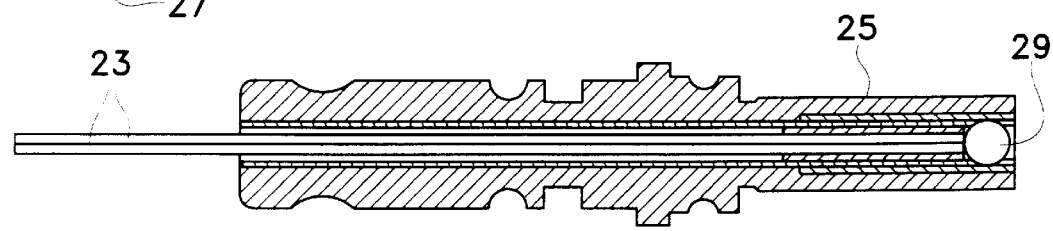
FIG. 3A is a cross-sectional view of a proximal connector of the optical fiber cable of FIG. 3.
Figure 3B:
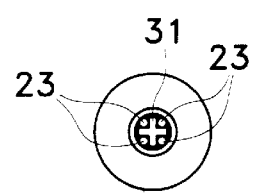
FIG. 3B is an end view of the distal connector of the optical fiber cable of FIG. 3.

Referring now to FIG. 3, there is shown a multi-spot laser delivery system 21 of the present invention. It is preferred in this system that optical fiber cable 48 be a multiple-fiber assembly, with the result that multiple spots can be imaged onto the treatment area. Moreover, the spacing of the fibers can be optimized to yield a more uniform geometric pattern. The surgeon using the system of FIGS. 1 and 2 can position the multi-spot pattern using the low power aiming beam and deliver the photocoagulative laser pulse. The time to position the multi-spot pattern is the same as the single spot procedure used in the prior art. However, the total treatment time is reduced by the number of spots in the pattern. As an example, if four (4) spots (as indicated in FIG. 3 by the four separate optical fibers 23) are used the treatment time is potentially reduced to one fourth the standard time.

Optical fiber cable 48 is constructed of four fibers 23 connected to the laser source via a proximal connector 25 (input end) and to the slit lamp imaging optics described above via a distal connector 27 (output end). The size of the fiber is chosen for the highest core to cladding diameter ratio for optimum energy collection at the proximal end. The maximum size of the fiber is governed by the magnification range of the imaging optics in the slit lamp and the desired spot size on the retina. Magnification ranges for standard SL imaging optics are 1:1 to 20:1. If the fibers selected are 200 microns in diameter, the imaging size on the retina would vary from 200–4000 microns. For PRP procedures, the surgeon typically uses a 500 micron spot. To insure uniform input of laser energy into the fibers, a lens 29 is provided in the optical path in the proximal connector. The lens shown is a ball lens; however, other types of focusing elements could be used.

A star spacer 31 is used at the distal end of distal connector 27 to provide a uniform spacing of two (2) times the spot diameter. The spacer can be metallic, ceramic, etc., or the fibers can be held in spaced relationship in an epoxy matrix material.

Figure 4:
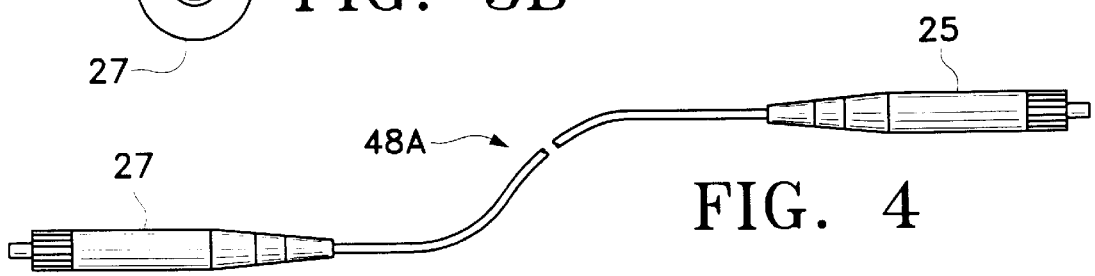
FIG. 4 is an elevation of an alternative embodiment of the optical fiber cable used in the system of FIG. 1.
Figure 4A:
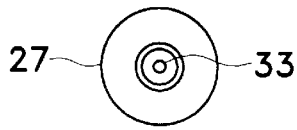
FIG. 4A is an end view of a distal connector of the optical fiber cable of FIG. 4, with parts removed for clarity.
Figure 4B:
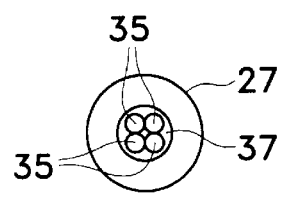
FIG. 4B is an end view similar to FIG. 4A with the removed parts reinserted.
Figure 4C:
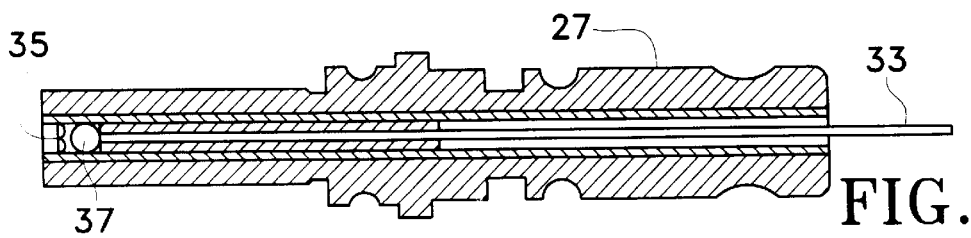
FIG. 4C is a longitudinal sectional view of the distal connector of the optical fiber cable of FIG. 4.

Referring to FIG. 4, an alternative optical cable assembly 48A for use with a slit-lamp assembly is shown. In cable 48A, there is a single fiber 33 optically connected to the laser source via proximal connector 25 (input end) and to the slit lamp imaging optics via distal connector 27 (output end). The proximal end of fiber 33 is a standard polished end fiber with no additional lenses. The distal end contains a microlens array 35 with four elements to produce four spots. A collimating lens 37 provides uniform light energy to the microlens array. The size of the fiber is chosen for the optimum energy collection at the distal end of the fiber. The lenses shown are a ball lens and a 4-element microlens array; however, other types of focusing elements could be used. The single laser beam transmitted by fiber 33 is collimated by lens 37 and split into four simultaneous parallel laser beams by microlens array 35 for application through the slit-lamp apparatus to the patient.

Referring to FIG. 5, another alternative construction of cable 48, labeled 48B, is illustrated. In this construction, the single laser beam from the source is split using fiber splitters. Specifically, in the embodiment shown in FIG. 5, cable 48B has a single optical fiber 33 connected to the laser source via proximal connector 25, which is multiplexed by means of a 1×4 multimode coupler 39 into four fibers 23 at the distal end. The proximal end is a standard polished end fiber with no additional lenses. Inside the multimode coupler the single fiber is multiplexed into four fibers via three 1:2 fiber splitters (disposed in a configuration such as that shown in FIG. 8A). Of course the actual method of splitting may be varied as desired.

The maximum size of the fiber is governed by the magnification range of the imaging optics in the slit lamp and the desired spot size on the retina. Magnification ranges for standard SL imaging optics are 1:1 to 20:1. If the fibers selected are 200 microns in diameter, the imaging size on the retina would vary from 200–4000 microns, as desired by the physician. Star spacer 31 is preferably used at the distal end to provide the desired spacing between the spots by holding the fibers 23 in fixed geometrical relationship.

Figure 7:
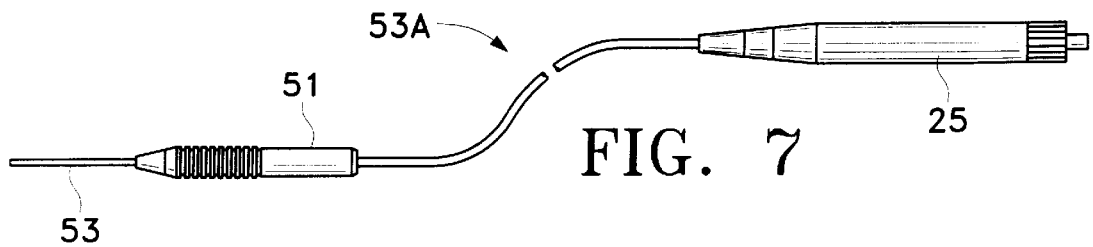
FIG. 7 is an elevation of an alternative embodiment of the laser probe of FIG. 6.
Figure 7A:
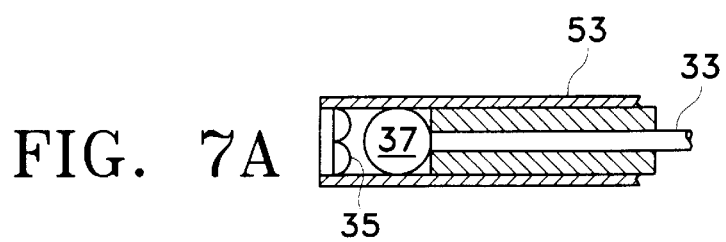
FIG. 7A is a cross sectional view of the distal end of the probe of FIG. 7.
Figure 8:
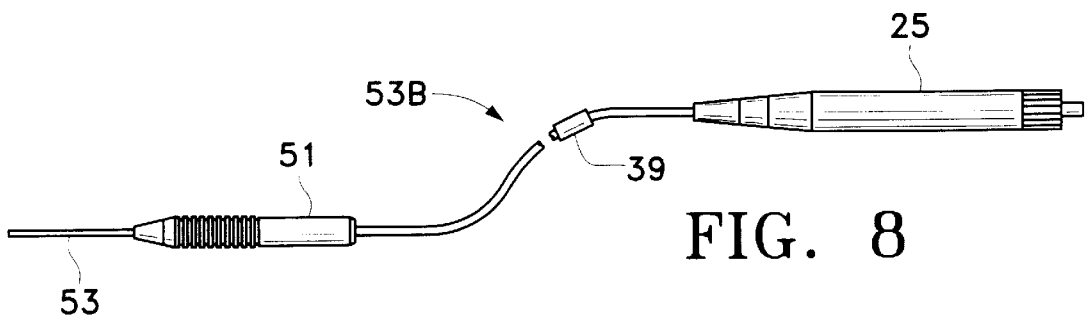
FIG. 8 is an elevation of a third embodiment of the laser probe of FIG. 6.
Figure 8A:
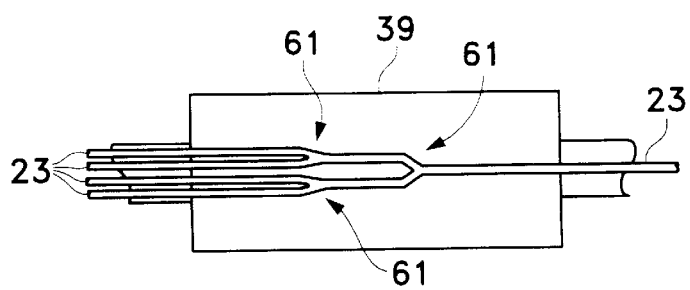
FIG. 8A is an enlarged view of a portion of the probe of FIG. 8.
Figure 8B:
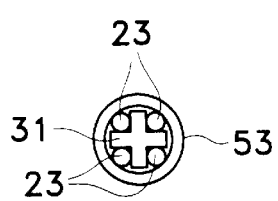
FIG. 8B is a distal end view of the probe of FIG. 8, with parts removed for clarity.
Figure 8C:
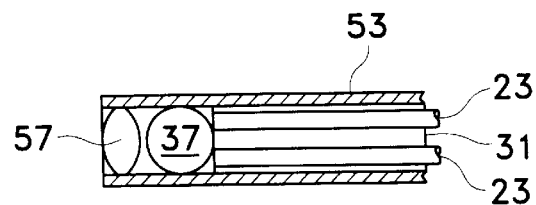
FIG. 8C is a cross sectional view of the distal end of the probe of FIG. 8.

As discussed above, when PRP treatment requires surgical intervention, the slit-lamp assembly of FIGS. 1 and 2 is not used. Rather endo-ocular laser probes such as those shown in FIGS. 6–8 are utilized. The optical constructions of these probes are very similar to the optical cable constructions discussed above. Rather than a distal connector, however, such probes have a handpiece 51, generally terminating in a distal needle 53.

By replacing the existing single fiber endo-laser probe with a multiple fiber probe (or other beam splitting devices discussed below), multiple spots are imaged onto the treatment area. The spacing of the fibers (and/or beams) can be optimized to yield a more uniform geometric pattern than is available with conventional equipment. The surgeon can position the multi-spot pattern using the low power aiming beam and deliver the photocoagulative laser pulse. The time to position the multi-spot pattern is generally the same as the single spot procedure, but the total treatment time is reduced by the number of spots in the pattern, similar to the reduction discussed above in connection with the slit-lamp system.

In FIG. 6, a probe 53 is constructed of four fibers 23 connected to the laser source via proximal connector 25. Fibers 23 run the entire length of probe 53 and terminate distally in handpiece 51. The size of the fibers is chosen for the highest core to clad diameter ratio for optimum energy collection at the proximal end. To insure uniform input of laser energy into the fibers, lens 29 is provided at the proximal end. Although the lens shown is a ball lens, other types of focusing elements could be used. Star spacer 31 is used at the distal end to provide the desired spacing of the fibers and to hold them in fixed geometrical relationship. A collimating lens 37 and/or a focusing lens 57 are preferably disposed distally of the fibers 23 to more accurately direct the resulting simultaneous laser beams.

In FIG. 7, an alternative embodiment 53A of the laser probe is shown. In this embodiment, the probe uses a single fiber 33 connected to the laser source via proximal connector, which fiber continues to the distal needle end of handpiece 51. The proximal end of fiber 33 is a standard polished end fiber with no additional lenses. The distal end terminates at a microlens array 35 having four elements to produce four spots at a distance to minimize risk of retinal tears. A collimating lens 37 provides uniform light energy to the microlens array. The lenses shown here are a ball lens and a 4-element microlens array, however, other types of focusing elements could be used.

In FIG. 8, a third embodiment 53B of the laser probe is shown. In this embodiment, a single fiber 33 is connected to the laser source via proximal connector 25 and is multiplexed by a 1×4 multimode coupler 39 into four fibers 23 at the distal end. The proximal end is a standard polished end fiber with no additional lenses. Inside the multimode coupler the single fiber is multiplexed into four fiber via three 1:2 fiber splitters 61, or by any other suitable method. The size of the spot and spot spacing vary proportionally with the distance from the distal tip to the retina. A star spacer 31 is used at the distal end to suitably space fibers 23. A collimating lens 37 and a focusing lens 57 may be provided distally to suitably focus the simultaneous laser beams at a distance from the distal end of the handpiece needle to help avoid the possibility of retinal tears.

It should be understood that the present invention does not depend on the particular type of laser being used, although the materials making up the optical fibers could be optimized for particular laser types. It is desired, however, that if practicable the optical fibers be chosen to have an optimum core to clad ratio. Various lens types, such as Gradient-Index (GRIN), ball diffractive, holographic, microlenslets, or any combination thereof may be used without changing the underlying invention. Moreover, although the invention has been described in connection with ophthalmic surgery, and in particular in connection with PRP, it should be understood that the invention may also have application to other procedures such as corneal ablation and/or cutting and dermatology.

What is claimed is:

1. A laser probe assembly, comprising:
   (a) a proximal connector for connecting the laser probe assembly to a laser source;
   (b) a distal connector for connecting the laser probe assembly to a laser delivery system;
   (c) a fiber optic cable optically connecting the proximal connector to the distal connector so as to create an optical path between the laser source and the laser delivery system;
   (d) a microlens array located in the distal connector near a distal end of the fiber optic cable; and
   (e) a collimating lens in the distal connector arranged between the distal end of the fiber optic cable and the microlens array.

2. A laser probe assembly, comprising:
   (a) a proximal connector for connecting the laser probe assembly to a laser source;
   (b) a distal connector for connecting the laser probe assembly to a laser delivery system;
   (c) a fiber optic cable having a plurality of optical fibers optically connecting the proximal connector to the distal connector so as to create an optical path between the laser source and the laser delivery system;
   (d) a first lens located on a proximal end of the proximal connector between the laser source and the fiber optic cable;
   (e) a second lens located at a distal end of the distal connector; and
   (f) a means in the distal connector for holding the optical fibers in a fixed geometric relationship.

3. A laser probe assembly, comprising:
   (a) a proximal connector for connecting the laser probe assembly to a laser source;
   (b) a handpiece terminating in a distal needle;
   (c) a fiber optic cable optically connecting the proximal connector to the handpiece so as to create an optical path between the laser source and the distal needle;
   (d) a microlens array located in the distal needle near a distal end of the fiber optic cable; and
   (e) a collimating lens in the distal needle arranged between the distal end of the fiber optic cable and the microlens array.

4. A laser probe assembly, comprising:
   (a) a proximal connector for connecting the laser probe assembly to a laser source;
   (b) a handpiece terminating in a distal needle;
   (c) a fiber optic cable having a plurality of optical fibers optically connecting the proximal connector to the handpiece so as to create an optical path between the laser source and the distal needle;
   (d) a first lens located on a proximal end of the proximal connector between the laser source and the fiber optic cable;
   (e) a second lens located at a distal end of the distal handpiece; and
   (f) a means in the distal needle for holding the optical fibers in a fixed geometric relationship.

* * * * *